US012741921B2

(12) United States Patent
Sandiri et al.

(10) Patent No.: US 12,741,921 B2
(45) Date of Patent: Sep. 22, 2026

(54) PROCESS FOR THE PRODUCTION OF ETHYL TERTIARY BUTYL ETHERS

(71) Applicant: HINDUSTAN PETROLEUM CORPORATION LIMITED, Hoskote Taluk (IN)

(72) Inventors: Santhoshkumar Reddy Sandiri, Hoskote Taluk (IN); Bennet Chelliahn, Hoskote Taluk (IN); Valavarasu Gnanasekaran, Hoskote Taluk (IN); Ramachandra Rao Bojja, Hoskote Taluk (IN)

(73) Assignee: HINDUSTAN PETROLEUM CORPORATION LIMITED (IN)

( * ) Notice: Subject to any disclaimer, the term of this patent is extended or adjusted under 35 U.S.C. 154(b) by 549 days.

(21) Appl. No.: 18/273,744

(22) PCT Filed: Mar. 17, 2021

(86) PCT No.: PCT/IN2021/050271
§ 371 (c)(1),
(2) Date: Jul. 21, 2023

(87) PCT Pub. No.: WO2022/157795
PCT Pub. Date: Jul. 28, 2022

(65) Prior Publication Data

US 2024/0101501 A1 Mar. 28, 2024

(30) Foreign Application Priority Data

Jan. 22, 2021 (IN) ............................ 202141003221

(51) Int. Cl.
*C07C 43/04* (2006.01)

(52) U.S. Cl.
CPC ................................ *C07C 43/046* (2013.01)

(58) Field of Classification Search
CPC ............................ C07C 41/06; C07C 43/046
See application file for complete search history.

(56) References Cited

U.S. PATENT DOCUMENTS

| | | | | |
|---|---|---|---|---|
| 3,726,942 | A | 4/1973 | Louder | |
| 4,440,963 | A | 4/1984 | Childs | |
| 5,569,787 | A | 10/1996 | Rastelli et al. | |
| 7,399,892 | B2 | 7/2008 | Rix | |
| 9,657,245 | B2 | 5/2017 | Ding | |
| 2008/0132730 | A1* | 6/2008 | Manzer | C07C 5/03 585/703 |

FOREIGN PATENT DOCUMENTS

| | | | | |
|---|---|---|---|---|
| CN | 101195560 | B | 6/2008 | |
| DE | 102006057856 | A1 * | 6/2008 | C07C 41/06 |

OTHER PUBLICATIONS

Hwang et al., "Azeotrope breaking for the system ethyl tert-butyl ether (ETBE) + ethanol at 313.15 K and excess properties at 298.15 K for mixtures of ETBE and ethanol with phosphonium-based ionic liquids" 2013.

* cited by examiner

*Primary Examiner* — Pancham Bakshi

(57) ABSTRACT

The present disclosure relates to a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1. The present disclosure also discloses a process of separating ethanol and ethyl tert-butyl ether. Further, the present disclosure discloses a composition comprising ethyl tert-butyl ether with a purity in the range of 91%-93%.

5 Claims, 2 Drawing Sheets

PROCESS FOR THE PRODUCTION OF ETHYL TERTIARY BUTYL ETHERS

FIELD OF INVENTION

The present disclosure broadly relates to a process of preparing oxygenates for fuel additive and particularly relates to a process for preparation of ethyl tert-butyl ether (ETBE) and its separation from ethanol (EtOH).

BACKGROUND OF INVENTION

In order to improve the anti-knocking properties of gasoline, refineries are looking for higher octane gasoline additives. Presently continuous catalytic reforming (CCR) aromatic product and fluid catalytic cracking (FCC) olefinic naphtha are mixed in the gasoline pool to improve the octane number. For example, U.S. Pat. No. 9,657,245B2 relates to producing low sulfur high octane number gasoline.

As the specifications are imposed on aromatics and olefinic content in the gasoline, addition of oxygenates has become unavoidable to meet the Euro-VI gasoline specifications. Oxygenates such as methyl tert-butyl ether (MTBE), ethyl tert-butyl ether (ETBE), tertiary amyl methyl (TAME) ether are classified as fuel additives that contain oxygen usually in the form of alcohol or ether. They generally have high octane number and low Reid vapor pressure (RVP), which helps in enhancing the fuel combustion, thereby reducing the fuel exhaust emissions. For instance, U.S. Pat. No. 3,726,942 relates to a process of producing 2-methyl-2-methoxypropane and alkylate from a stream of mixed C4's wherein the said stream is first dehydrogenated and then fed to an etherification unit along with methanol to form 2-methyl-2-methoxypropane. Subsequently, water is used to remove methanol from 2-methyl-2-methoxypropane by washing it with water.

Among the mentioned oxygenates, ETBE is majorly preferred over MTBE due to the fact that MTBE being highly soluble in water, often leads to causing ground water contamination by possible spills or leakage of gasoline at the gas-stations.

ETBE is generally produced by an etherification reaction of C4 hydrocarbons mixture and ethanol. After the reaction completes, the remaining amount of unreacted ethanol generally gets mixed with the ETBE and forms an azeotrope. The existence of the ETBE/ethanol azeotrope makes it difficult to separate ethanol from ETBE to meet the specifications for permitted ethanol content in gasoline. Although, extensive research has been devoted to this field and several methods have been developed to prepare ETBE, there are still many setbacks and difficulties faced in separating and purifying it to make it useful as a fuel additive. Additionally, most of the available methods involve multiple steps that are not only complex to perform but also incur additional costs to the manufacturer.

U.S. Pat. No. 7,399,892 discloses a process for preparing low-water ethanol from at least two streams of relatively water-rich ethanol that have a different water content by dewatering at membranes. The low-water ethanol is then used to prepare ethyl tert-butyl ether (ETBE).

Despite the several efforts made, the available processes still suffer the drawback of not being able to produce substantially pure ETBE. Contaminated ETBE is less effective in improving the octane number of gasoline and require further purification steps to be useful. Moreover, the steps also require additional energy input which makes the overall process energy inefficient and costly. Hence, there arises a dire need in the state of the art to provide a suitable process for production of ETBE that is not only simple and effective in producing ETBE but is also economical both in terms of energy requirement and the overall cost.

SUMMARY OF THE INVENTION

In a first aspect of the present disclosure, there is provided a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene (IB), and the ethanol to isobutylene mole ratio is in the range of 1:1 to 2:1.

In a second aspect of the present disclosure, there is provided a process for separation of ethanol and ethyl tert-butyl ether, the process comprising: (a) feeding an entrainer to a feed comprising ethyl-tert-butyl ether and ethanol; and (b) separating ethanol and ethyl-tert-butyl ether, wherein the ethyl-tert-butyl ether and the entrainer ratio is in the range of 30:1 to 10:1.

In a third aspect of the present disclosure, there is provided a composition comprising: (i) ethyl tert-butyl ether with a purity in the range of 91-93% as prepared by the process comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1; (ii) ethanol; and (iii) the entrainer.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
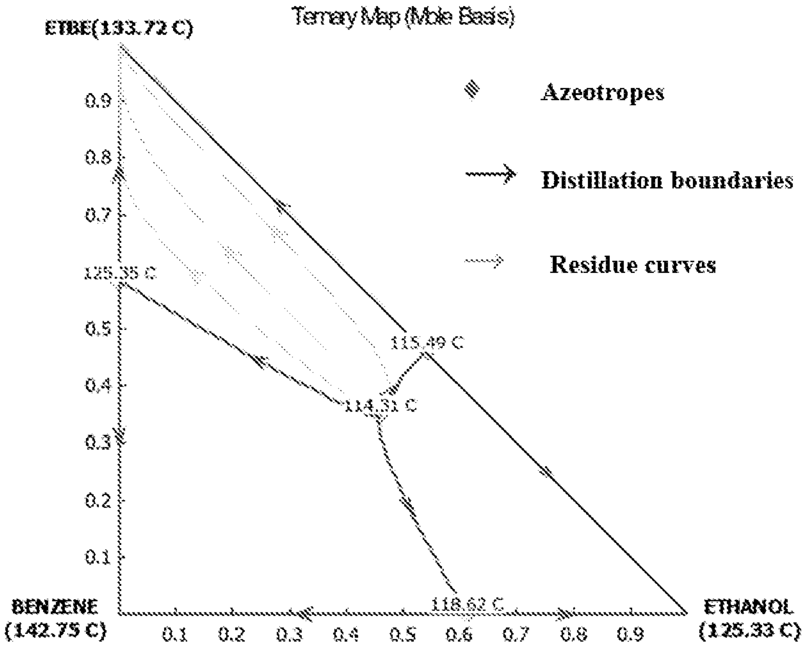
FIG. 1 depicts the ternary azeotrope map of a ternary azeotrope formed between the benzene, ETBE and ethanol (EtOH), in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a pressure range of about 15-30 bar should be interpreted to include not only the explicitly recited limits of about 15 bar to about 30 bar, but also to include sub-ranges, such as 15-20 bar, 20-30 bar, and so forth, as well as individual amounts, including fractional amounts, within the specified ranges, such as 24.5 bar, and 24.252 bar, for example.

The term "octane number" used herein also refers to antiknock rating, which is a measure of the compression that a fuel can withstand before detonating. It also refers to the ability of a fuel to resist knocking when ignited in a fuel mixture with air in an engine. Lower octane number leads to engine knocking which is undesirable.

The term "anti-knock agent" used herein refers to a gasoline additive used to reduce engine knocking and increase the fuel's octane number by raising the temperature and pressure at which auto-ignition occurs.

The term "Euro-VI gasoline specifications" used herein refers to the European emission standards defining the acceptable limits for exhaust emissions of new vehicles sold in the European Union and EEA member states.

The term "entrainer" used herein refers to a separating agent that is added to a binary azeotrope of two close boiling liquids.

The term "azeotrope" used herein refers to a mixture of at least two liquids (ETBE and ethanol in the present disclosure) having close boiling points, however, the azeotrope resulting from them exhibits a constant boiling point at a specific composition (mole %) of the liquids. This boiling point may be higher or lower than the boiling points of the two liquids.

The term "low boiling azeotrope" used herein refers to an azeotrope that has a lower boiling point than the boiling point of both the liquids forming the azeotrope.

The term "Reid vapour pressure" used herein refers to the pressure of gasoline vapor exerted at at 37.8° C. (100° F.) as determined by the test method ASTM-D-323. It is commonly used to measure the volatility of gasoline.

The term "purge rate" used herein refers to the feed rate in kg/hr of the entrainer.

The term "reboiler energy" used herein refers to the energy input used by the reboiler in the distillation column.

The term "condenser energy" used herein refers to the energy input used by the condenser in the distillation column.

The term "weight hourly space velocity" used herein refers to the weight of feed (ethanol, entrainer) flowing per unit weight of the catalyst per hour loaded in the fluid micro bed reactor.

The term "isobutylene conversion" used herein refers to the conversion of isobutylene into ethyl tert-butyl ether.

The term "C4 hydrocarbon" used herein refers to the hydrocarbon stream comprising isobutylene (5-40 wt %), propane, isobutane, n-butane, 1-butene, cis-2-butne, isobutene, trans-2-butene, n-pentane, and isopentane.

The term "reformate stream" used herein refers to refinery consisting of benzene, toluene, xylene and C9 aromatic mixtures.

The phrase "mixture of benzene and n-hexane" used herein may also be FCC heart cut naphtha.

The density of benzene used herein is 876 kg/$m^3$ and the density of n-hexane used herein is 655 kg/$m^3$.

The term "catalyst" used herein refers to chemical compounds used for catalyzing the etherification reaction of isobutylene with ethanol to form ETBE. The catalyst may be zeolite catalyst, acid catalyst, selected from non-limiting examples including, ZSM-5, amberlyst 15, amberlyst 35, amberlyst 16, amberlyst 36, amberlyst 39, amberlyst 40, amberlyst 45, amberlyst 46, amberlyst 48, amberlyst DT, Purolite CT-124, Purolite CT-175, Purolite CT-275, Purolite CT-482, Purolite MN-500, aluminosilicates, H-beta zeolite, ZSM-5, ZSM-57, lewatit K 2629, silicotungstic acid, and tungstophosphoric acid.

As discussed in the background, oxygenates are generally used as anti-knocking agents in gasoline to increase its octane number. Some of the commonly used oxygenates include MTBE, ETBE and TAME. However, both the oxygenates except for ETBE are associated with certain drawbacks. Methyl tertiary butyl ether (MTBE) is a high-octane gasoline additive, however, it is easily soluble in water (with solubility of 4.3 g/100 ml water as shown in Table 1) and has high Reid vapor pressure which makes it less desirable as a gasoline additive. On the other hand, while tertiary amyl methyl ether (TAME) has less Reid vapor pressure, it consumes amylenes as a raw material, where amylenes itself are good research octane number (RON) boosters used in the refinery. Contrary to above mentioned issues of MTBE and TAME, ETBE shows advantageous properties of low Reid vapor, high octane number and low water solubility. In view of these properties, the present disclosure focuses on preparing ethyl tert-butyl ether (ETBE), which can be used further as an oxygenate for fuel additive.

The present disclosure relates to a process of preparing ethyl tert-butyl ether (ETBE), having an initial step of reacting ethanol with a mixture of $C_4$ hydrocarbon feed in the presence of a catalyst wherein, the mixture of $C_4$ hydrocarbon feed comprises isobutylene (IB), and the ethanol to isobutylene mole ratio is in the range of 1:1 to 2:1. The isobutylene reacts with ethanol and undergoes etherification to form ETBE as the product. However, since ethanol is taken in excess in the reaction mixture, the unreacted ethanol leads to the formation of a low boiling binary azeotrope with ETBE. To this binary azeotrope, an entrainer is added which forms a ternary azeotrope with ETBE and ethanol. The entrainer is added in the upstream of the reactor which helps in the efficient separation of the ETBE-ethanol binary azeotrope. The high pressure is employed to keep the reactant in a liquid phase. As the etherification reaction between ethanol and IB is an exothermic equilibrium reaction, maintaining such a lower temperature range and keeping the ethanol to IB mole ratio in the range of 1:1 to 2:1, wherein ethanol is kept in excess, enables the reaction to move in forward direction to give high isobutylene conversion rate of more than 85 wt. % and therefore, results in high ETBE yield as well.

Further to above, the most challenging issue of compromised purity of ETBE faced in the prior art is also overcome in the present disclosure. The ETBE formed in the first step forms an azeotrope with unreacted ethanol which makes the separation of pure ETBE difficult from the ethanol. The azeotropic concentration of ETBE and ethanol is 0.46 and 0.54 mole fractions respectively. Having such a high concentration of ETBE in the recycle stream will cause an increase in the operational cost and is not economically viable to recycle it to reactor. Moreover, the content of ethanol must also be reduced to qualify the specifications related to the ethanol content in gasoline. Therefore, with an aim to provide a suitable technique for separating the EBTE-ethanol azeotrope to produce substantially pure ETBE, the disclosed process includes addition of an entrainer which may be selected from benzene, n-hexane, pentane, cyclohexane, cyclopentane, toluene, reformate stream, heart cut naphtha steam, or their combinations to form a mixture. These specified entrainers form a low-boiling ternary azeotrope with ETBE and ethanol that aids in the separation of ethanol from ETBE and renders highly pure ETBE of purity in the range of 91-93%. The details of the boiling point of each of the entrainer and the lowered boiling point of the resulting azeotrope with ethanol, along with the mole % of the entrainer in the azeotrope is presented in Table 2 below, based on which the mentioned entrainers were selected for the purpose of this disclosure. For example, a mixture of benzene and n-hexane may be combined in the volume ratio range of 90:10 to 40:60 which is sufficient enough for an efficient separation with added advantage of highly reduced operational cost. Hence, the present disclosure also discloses a process of separating ethanol and ethyl tert-butyl ether, wherein the ethyl-tert-butyl ether and the entrainer ratio is maintained in the range of 30:1 to 10:1. The feeding rate of the entrainer is kept in the range of 0-250 kg/hr which is significantly low as compared to the available methods and is also sufficient to recover about 70-90% of ETOH from ETBE and recycle back to the reactor. In addition to above, the overhead distillation stream comprising the entrainer, ETBE and EtOH is also recycled back to the reaction mixture with a flow rate of 1790-1961 kg/hr in order to utilize the ethanol in the next etherification reaction. The amount of ethanol in the recycle stream is highly reduced to only 3% which shows the high efficiency of the present entrainers in separating ethanol from ETBE. The present disclosure also demonstrates improved efficiency in terms of low energy demands as the reboiling energy and condensation energy of only 4280 KW and 4173 KW respectively, is consumed which is substantially lower than energy consumed in the available processes. The present disclosure further relates to a composition comprising the ethyl tert-butyl ether obtained in high purity (910%-93%) after separation from ethanol, and residual quantities of ethanol and entrainer. Overall, the present disclosure provides a simple and convenient process for preparing the much-demanded fuel additive, ethyl tert-butyl ether having high purity, wherein the process does not create additional burden of high energy demands and thereby, is highly economical and feasible to scale up to manufacturing ETBE at industrial levels for further commercialization.

TABLE 1

| PROPERTY | MTBE | TAME | ETBE |
|---|---|---|---|
| RVP, (psi) | 8.0 | 2.5 | 4.4 |
| RON | 118 | 111 | 118 |
| Boiling point (° C.) | 55 | 86 | 73 |
| Oxygen content (wt %) | 18.2 | 15.7 | 15.7 |
| Solubility in water (g/100 ml water) | 4.3 | 1.15 | 1.20 |

TABLE 2

| S. No | Component | Pure component boiling point, ° C. | Azeotrope boiling temperature, ° C. | Mole % |
|---|---|---|---|---|
| 1 | ETBE | 69-71 | 66.6 | 0.79 |
| 2 | Cyclopentane | 49 | 44.7 | 0.11 |
| 3 | Pentane | 36.1 | 34.3 | 0.08 |
| 4 | Benzene | 80.1 | 67.9 | 0.44 |
| 5 | Cyclohexane | 80.74 | 64.8 | 0.43 |
| 6 | Hexane | 68 | 58.7 | 0.33 |

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1. In one another embodiment of the present disclosure, the contacting the mixture with the entrainer is carried out at a temperature in the range of 45-65° C. and a pressure in the range of 16-25 bars to obtain ethyl tert-butyl ether, wherein, the mixture of $C_4$ hydrocarbon feed comprises isobutylene, and the ethanol to isobutylene mole ratio is in the range of 1.1:1 to 1.8:1. In yet another embodiment of the present disclosure, the contacting the mixture with the entrainer is carried out at a temperature in the range of 50-60° C. and a pressure in the range of 18-21 bars to obtain ethyl tert-butyl ether, wherein, the mixture of $C_4$ hydrocarbon feed comprises isobutylene, and the ethanol to isobutylene mole ratio is in the range of 1.15:1 to 1.7:1. In one another embodiment of the present disclosure, the contacting the mixture with the entrainer is carried out at a temperature in the range of 50-60° C. and a pressure in the range of 18-21 bars to obtain ethyl tert-butyl ether, wherein, the mixture of $C_4$ hydrocarbon feed comprises isobutylene, and the ethanol to isobutylene mole ratio is in the range of 1.1:1 to 1.6:1.

In an embodiment of the present disclosure, there is provided a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer selected from benzene, n-hexane, pentane, cyclohexane, cyclopentane, toluene, reformate stream, heart cut naphtha steam, or mixtures thereof, at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1.

In an embodiment of the present disclosure, there is provided a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer selected from benzene, n-hexane, toluene, or a mixture of benzene and n-hexane at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1. In one another embodiment of the present disclosure, the entrainer is benzene. In yet another embodiment of the present disclosure, the entrainer is n-hexane. In one another embodiment of the present disclosure, the entrainer is a mixture of benzene and n-hexane. In yet another embodiment of the present disclosure, the entrainer is toluene. In one another embodiment of the present disclosure, the entrainer is a mixture of toluene and xylene.

In an embodiment of the present disclosure, there is provided a process for the preparation of ethyl tert-butyl ether comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene, the ethanol to isobutylene mole ratio is in the range of 1:1 to 2:1, and the entrainer is a mixture of benzene and n-hexane in the volume ratio range of 90:10 to 40:60. In one another embodiment of the present disclosure the entrainer is a mixture of benzene and n-hexane in the volume ratio range of 85:15 to 50:50. In yet another embodiment of the present disclosure the entrainer is a mixture of benzene and n-hexane in the volume ratio range of 82:18 to 75:25.

In an embodiment of the present disclosure, there is provided a process for the preparation of ethyl tert-butyl ether as described herein, wherein the entrainer is a mixture of benzene and n-hexane in the weight ratio range of 7884:655 to 3504:3930.

In an embodiment of the present disclosure, there is provided a process for the preparation of ethyl tert-butyl ether comprising: (a) reacting ethanol with a mixture of $C_4$ hydrocarbon feed in the presence of a catalyst selected from amberlyst 15, amberlyst 35, amberlyst 16, amberlyst 36, amberlyst 39, amberlyst 40, amberlyst 45, amberlyst 46, amberlyst 48, amberlyst DT, Purolite CT-124, Purolite CT-175, Purolite CT-275, Purolite CT-482, Purolite MN-500, aluminosilicates, H-beta zeolite, ZSM-5, ZSM-57, lewatit K 2629, silicotungstic acid, tungstophosphoric acid, and combinations thereof to obtain a mixture; and (b) contacting the mixture with an entrainer selected from benzene, n-hexane, pentane, cyclohexane, cyclopentane, toluene, reformate stream, heart cut naphtha steam, or mixtures thereof at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1. In one another embodiment of the present disclosure, the catalyst is amberlyst 35 and the entrainer is selected from benzene, n-hexane, toluene, mixture of benzene and n-hexane, or mixture of toluene and xylene. In yet another embodiment of the present disclosure, the catalyst is amberlyst 35 and the entrainer is a mixture of benzene and n-hexane.

In an embodiment of the present disclosure, there is provided a process for the preparation of ethyl tert-butyl ether as described herein, wherein the process provides 85-97% conversion of isobutylene. In another embodiment of the present disclosure, the process provides 89-93% conversion of isobutylene.

In an embodiment of the present disclosure, there is provided a process for the preparation of ethyl tert-butyl ether as described herein, wherein the entrainer forms a low boiling azeotrope with the ethanol present in the mixture.

In an embodiment of the present disclosure, there is provided a process for the preparation of ethyl tert-butyl ether as described herein, wherein the entrainer and ethanol in the mixture are recycled.

In an embodiment of the present disclosure, there is provided a process for separation of ethanol and ethyl tert-butyl ether, the process comprising: (a) feeding an entrainer to a feed comprising ethyl-tert-butyl ether and ethanol; and (b) separating ethanol and ethyl-tert-butyl ether, wherein the ethyl-tert-butyl ether and the entrainer ratio is in the range of 30:1 to 10:1. In one another embodiment of the present disclosure, the ethyl-tert-butyl ether and the entrainer ratio is in the range of 25:1 to 13:1. In yet another embodiment of the present disclosure, the ethyl-tert-butyl ether and the entrainer ratio is in the range of 16:1 to 14:1.

In an embodiment of the present disclosure, there is provided a process for separation of ethanol and ethyl tert-butyl ether, the process as described herein, wherein the feeding the entrainer is carried out at a purge rate in the range of 0-250 kg/hr. In one another embodiment of the present disclosure, the feeding the entrainer is carried out at a purge rate in the range of 0.5-250 kg/hr. In yet another embodiment of the present disclosure, the feeding the entrainer is carried out at a purge rate in the range of 10-250 kg/hr. In one another embodiment of the present disclosure, the feeding the entrainer is carried out at a purge rate in the range of 50-250 kg/hr. In yet another embodiment of the present disclosure, the feeding the entrainer is carried out at a purge rate in the range of 100-250 kg/hr. In one another embodiment of the present disclosure, the feeding the entrainer is carried out at a purge rate in the range of 130-210 kg/hr. In yet another embodiment of the present disclosure, the feeding the entrainer is carried out at a purge rate in the range of 140-205 kg/hr.

In an embodiment of the present disclosure, there is provided a process for separation of ethanol and ethyl tert-butyl ether, the process comprising: (a) feeding an entrainer selected from benzene, n-hexane, pentane, cyclohexane, cyclopentane, toluene, reformate stream, heart cut naphtha steam, or mixtures thereof to a feed comprising ethyl-tert-butyl ether and ethanol; and (b) separating ethanol and ethyl-tert-butyl ether, wherein the ethyl-tert-butyl ether and the entrainer ratio is in the range of 30:1 to 10:1, and the feeding the entrainer is carried out at a purge rate in the range of 0-250 kg/hr. In one another embodiment of the present disclosure, the entrainer is selected from benzene, n-hexane, toluene, a mixture of benzene and n-hexane, or heart cut naphtha steam.

In an embodiment of the present disclosure, there is provided a process for separation of ethanol and ethyl tert-butyl ether, the process comprising: (a) feeding an entrainer to a feed comprising ethyl-tert-butyl ether and ethanol; and (b) separating ethanol and ethyl-tert-butyl ether, wherein the ethyl-tert-butyl ether and the entrainer ratio is in the range of 30:1 to 10:1, the feeding the entrainer is carried out at a purge rate in the range of 0-250 kg/hr, and the entrainer, ethanol, and ethyl tert-butyl ether form a low boiling azeotropic mixture.

In an embodiment of the present disclosure, there is provided a process for the preparation of ethyl tert-butyl ether comprising: (a) reacting ethanol with a mixture of $C_4$ hydrocarbon feed in the presence of Amberlyst-15 to obtain a mixture; and (b) contacting the mixture with an entrainer selected from benzene, n-hexane, toluene, or a mixture of benzene and n-hexane in the volume ratio of 0.91:0.30 (weight ratio 80:20), at a temperature in the range of 40-70° C. and a pressure in the range of 16-20 bars to obtain ethyl tert-butyl ether, wherein, the mixture of $C_4$ hydrocarbon feed comprises isobutylene (IB), and the ethanol to isobutylene mole ratio is 1.2:1, the process provides 86-96% conversion of isobutylene, the entrainer forms a low boiling azeotrope with the ethanol present in the mixture, and the entrainer and ethanol in the mixture are recycled.

In an embodiment of the present disclosure, there is provided a process for the preparation of ethyl tert-butyl ether comprising: (a) reacting ethanol with a mixture of $C_4$ hydrocarbon feed in the presence of Amberlyst-15 to obtain a mixture; and (b) contacting the mixture with an entrainer selected from benzene, n-hexane, toluene, or a mixture of benzene and n-hexane in the volume ratio 0.91:0.30 (weight ratio 80:20), at a temperature in the range of 40-70° C. and a pressure in the range of 16-20 bars to obtain ethyl tert-butyl ether, wherein, the mixture of $C_4$ hydrocarbon feed comprises isobutylene (IB), and the ethanol to isobutylene mole ratio is 1.6:1, the process provides 86-96% conversion of isobutylene, the entrainer forms a low boiling azeotrope with the ethanol present in the mixture, and the entrainer and ethanol in the mixture are recycled.

In an embodiment of the present disclosure, there is provided a process for separation of ethanol and ethyl tert-butyl ether, the process comprising: (a) feeding an entrainer selected from benzene, n-hexane, toluene, or a mixture of benzene and n-hexane in the volume ratio 0.91:0.30 (weight ratio 80:20) to a feed comprising ethyl-tert-butyl ether and ethanol; and (b) separating ethanol and ethyl-tert-butyl ether, wherein the ethyl-tert-butyl ether and the entrainer ratio is 15:1, the feeding the entrainer is carried out at a purge rate of 200 kg/hr, and the entrainer, ethanol, and ethyl tert-butyl ether form a low boiling azeotropic mixture.

In an embodiment of the present disclosure, there is provided a composition comprising: (i) ethyl tert-butyl ether with a purity in the range of 91-93% prepared by the process comprising: (a) reacting ethanol with a mixture of $C_4$ hydrocarbon feed in the presence of a catalyst to obtain a mixture; and (b) contacting the mixture with an entrainer at a temperature in the range of 40-70° C. and a pressure in the range of 15-30 bars to obtain ethyl tert-butyl ether, wherein, the mixture of $C_4$ hydrocarbon feed comprises isobutylene, and the ethanol to isobutylene mole ratio is in the range of 1:1 to 2:1; (ii) ethanol; and (iii) an entrainer.

In an embodiment of the present disclosure, there is provided a composition comprising: (i) ethyl tert-butyl ether with a purity in the range of 91-93% prepared by the process as described herein (ii) ethanol; and (iii) an entrainer selected from benzene, n-hexane, pentane, cyclohexane, cyclopentane, toluene, reformate stream, heart cut naphtha steam, or mixtures thereof. In one another embodiment of the present disclosure, the entrainer is benzene. In yet another embodiment of the present disclosure, the entrainer is n-hexane. In one another embodiment of the present disclosure, the entrainer is toluene. In yet another embodiment of the present disclosure, the entrainer is a mixture of benzene and n-hexane. In yet another embodiment of the present disclosure, the entrainer is a mixture of toluene and xylene. In one another embodiment of the present disclosure, the entrainer is heart cut naphtha steam.

Although the subject matter has been described in considerable detail with reference to certain examples and implementations thereof, other implementations are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Materials and Methods

For the purpose of present disclosure, the acid catalyst amberlyst 35 was obtained from Dow France S.A.S. The C4 hydrocarbon synthetic feed was obtained as refinery FCC unit C4 stream composition. The separation efficiency with different entrainers was studied using model developed in Aspen Hysys.

Example 1.1

Process for the Preparation of ETBE:

A fixed micro bed reactor was packed with 15 grams of Amberlyst 35 ion exchange resin (catalyst) and a C4 hydrocarbon feed, comprising isobutylene was fed to the reactor along with ethanol. The composition of the C4 hydrocarbon feed used herein is given in Table 3 below. An etherification reaction of the isobutylene with ethanol was allowed to occur to form ethyl tert-butyl ether. Various reactions (runs) were carried out at varied temperature and pressure conditions as illustrated in Table 4. The amount of total feed (C4 hydrocarbon feed and ethanol) was varied at different weight hourly space velocities (WHSV) thereby, varying the WHSV of the total isobutylene content and ethanol (EtOH+IB). The ethanol to IB ratio, as it is critical to achieve the desired isobutylene conversion %, was also varied in various runs.

TABLE 3

| Component | Wt % |
|---|---|
| Propane | 0.008 |
| Ethane | 0.0 |
| isobutane | 0.23 |
| n-Butane | 0.105 |
| 1-Butene | 0.122 |
| Cis-2-butene | 0.152 |
| isobutene | 0.183 |
| Trans-2-Butene | 0.203 |

TABLE 4

| RUN No. | R1 | R2 | R3 | R4 | R5 | R6 |
|---|---|---|---|---|---|---|
| Temperature, (° C.) | 40.0 | 50.0 | 60.0 | 70.0 | 50.0 | 70.0 |
| Pressure, (bar) | 16.0 | 20.0 | 20.0 | 20.0 | 17 | 18.0 |
| WHSV, EtOH + IB ($hr^{-1}$) | 1.48 | 1.50 | 1.48 | 1.52 | 1.73 | 1.72 |
| WHSV, total feed ($hr^{-1}$) | 6.1 | 6.1 | 6.1 | 6.1 | 6.5 | 6.3 |
| Ethanol/IB mole ratio | 1.21 | 1.24 | 1.21 | 1.26 | 1.55 | 1.58 |
| ETBE yield, (EtOH + IB) (wt %) | 77.23 | 73.14 | 73.48 | 70.55 | 79.70 | 69.33 |
| Isobutylene conversion (wt %) | 89.67 | 93.34 | 90.22 | 86.52 | 95.02 | 90.74 |

It can be observed from the runs R2, R3, and R4 in Table 4, that as the temperature of the reactor was increased, the isobutylene conversion decreased from 93.94 wt % to 86.52 wt %. Similarly, on decreasing the temperature from 50° C. to 40° C. in R2 and R3, the isobutylene conversion fell from 93.34% to 89.67%. Therefore, experiments were carried out between this temperature range. Further, on comparing R4 and R6 where the temperature was kept the same and the pressure was slightly varied, R6 showed a higher isobutylene conversion of 90.74 wt % in contrast to 86.52 wt % in R4. This result is attributed to the increased ethanol/IB mole ratio from 1.26 to 1.58 in R4 and R6 respectively. Similarly, the runs R2 and R5 also display the same trend as the ethanol/IB ratio increase from 1.21 to 1.55, also increases the isobutylene conversion rate. Hence, the above observations support the fact that the etherification reactions are exothermic equilibrium reaction, and thus, it can be inferred that a higher end of i.e., 40-70° C. temperature range, the mole ratio of ethanol/IB needs to be increased in order to achieve the desired isobutylene conversion rate. The yield of ETBE obtained in all the runs is comparable and has appreciably high magnitude of more than 69%. In addition to above, when the ratio of ethanol/IB ratio was reduced from 1:1, the isobutylene conversion rate also declined. On the other hand, ethanol/IB ratio greater than 1:2 lead to a higher ethanol content in the reactor effluent, which consumed higher hot/cold utilities to separate the ethanol from oxygenates product and significantly increased the operational expenses of the process. Therefore, the experimental runs performed under the disclosed ranges of temperature, pressure, and ethanol/IB mole ratio gave superior results both in terms of high ether yield and isobutylene conversion and helped in maintaining the operational cost as well.

Example 1.2

Separation of ETBE

Figure 2:
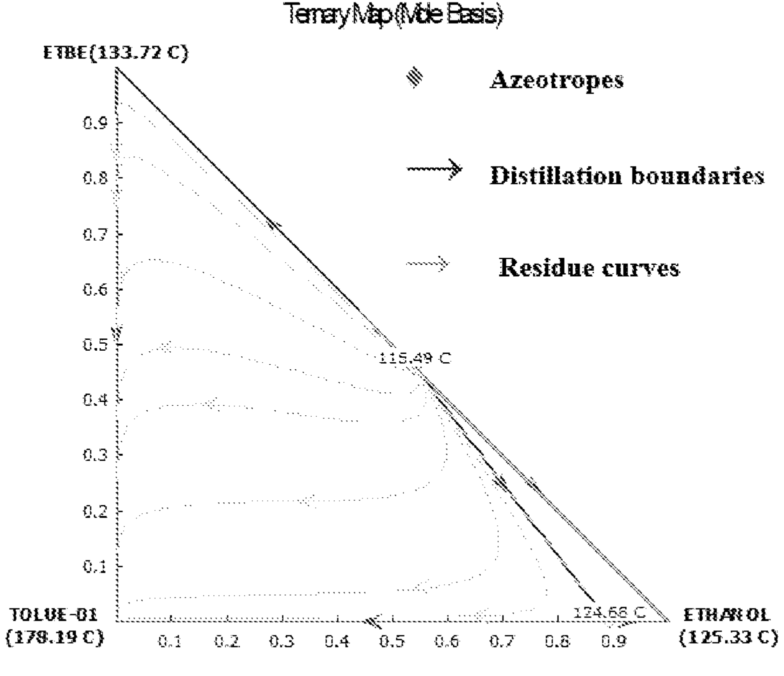
FIG. 2 depicts the ternary azeotrope map of a ternary azeotrope formed between the toluene, ETBE and ethanol (EtOH), in accordance with an embodiment of the present disclosure.
Figure 3:
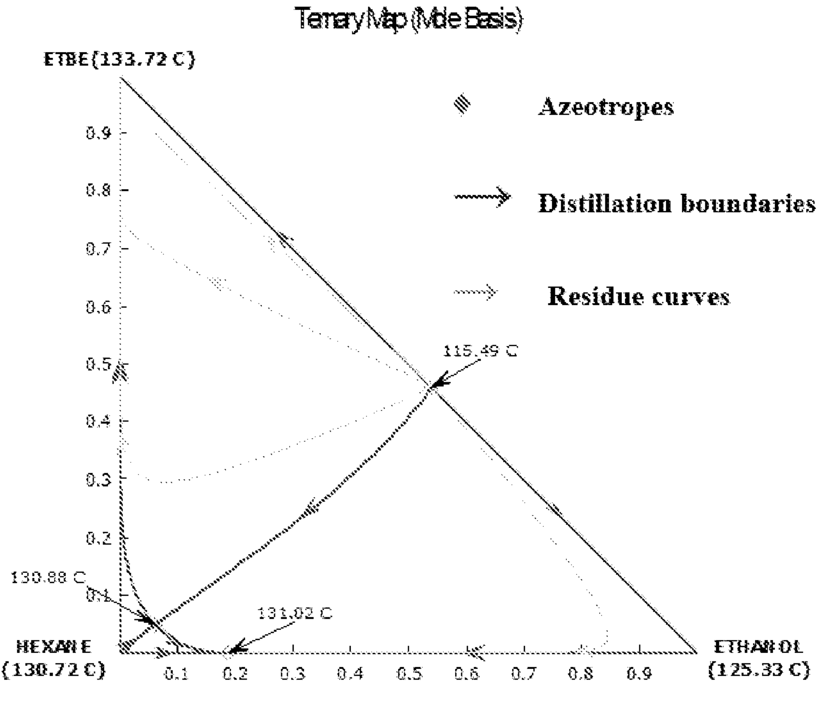
FIG. 3 depicts the ternary azeotrope map of a ternary azeotrope formed between the n-hexane, ETBE and ethanol (EtOH), in accordance with an embodiment of the present disclosure.
Figure 4:
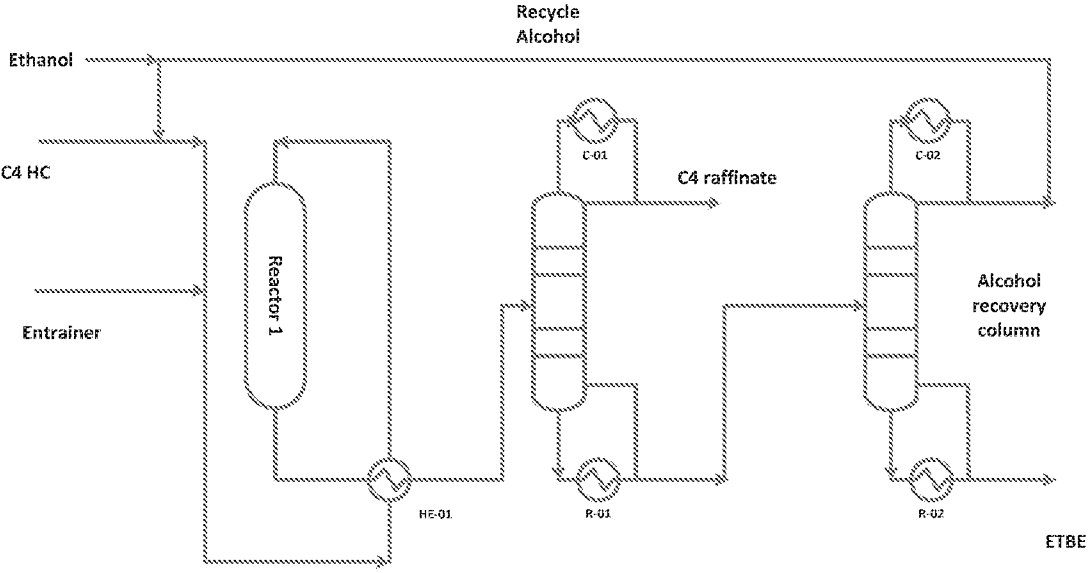
FIG. 4 depicts the process flow scheme for ETBE-ethanol etherification reaction and distillation with an entrainer, in accordance with an embodiment of the present disclosure.

In order to separate the ETBE from the ETBE-ethanol azeotrope formed in the reaction mixture, entrainers such as benzene, n-hexane, toluene, and a mixture of benzene (80 wt. %) and n-hexane (20 wt %) (working example) were added to form aternary azeotrope with the ETBE and ethanol. The ternary mole maps of ETBE-benzene-EtOH and ETBE-n-hexane-EtOH are shown in FIG. 1 and FIG. 3 respectively. In case of toluene (FIG. 2), the relative volatilities of ETBE and ethanol increases, which leads to better separation of ETBE and EtOH azeotrope. The process flow scheme for the ETBE-ethanol etherification reaction and separation with the entrainers described in the present disclosure including benzene, n-hexane, toluene, and mixture of benzene and n-hexane is depicted in FIG. 4, wherein the ethanol, C4 hydrocarbon feed, and the entrainer is fed to reactor 1. At the end of the process, pure ETBE is obtained from the bottom product and the alcohol is recycled back from the alcohol recovery system. The separation of ETBE was affected due to the formation of this ternary azeotrope where the low boiling azeotrope is drawn from the overhead stream and the pure ETBE is removed from the bottom product. The results for ETBE yield and energy consumption for different entrainers are provided in Table 5. In the comparative example, none of the entrainer selected from the laundry list as disclosed in the present disclosure was used. The rate of C4 hydrocarbon feed and ethanol feed was maintained at 9943 kg/hr and 1550 kg/hr respectively, so as to obtain the ethanol/IB ratio of 1.2:1. From the etherification reaction, 3300 kg/hr of ETBE was obtained, to which 200 kg/hr of the entrainer was added to maintain 15:1 ratio of ETBE and entrainer.

For the benzene entrainer, the composition of the ternary azeotrope at 3 bar was ETBE-37%, ethanol-40.3%, and benzene-22.4% (in mole %). The obtained azeotrope was then subjected to azeotropic distillation as a result of which, 3004 kg/hr of 91-93% pure ETBE (product) was achieved in the product and the % of residual ethanol was significantly reduced to 0.0334% by weight. The recycle stream flow rate (1961 kg/hr) and the purge rate (196.1 kg/hr) was also significantly less than the comparative example. Moreover, the reboiler energy and condenser energy was also observed to be consumed in very less amount of only 4379 KW and 4273 KW respectively. On the other hand, in the comparative example, lesser amounts of ETBE was obtained and the energy consumption was also much higher. The same pattern of results was observed for other entrainers as well, which is evident from data shown in Table 5 below. Therefore, it was clear that the disclosed entrainers provide an effective separation of excess EtOH from the oxygenates product (ETBE) and the excess EtOH and entrainer can be recycled back to the reactor for further utilization of unconverted EtOH in a cost-effective manner without consuming high amounts of energy in the process.

TABLE 5

| Measuring parameter | Comparative example | Working example |
|---|---|---|
| ENTRAINER - BENZENE + n-HEXANE | | |
| Feed rate, C4 hydrocarbon feed, (Kg/hr) | 9943 | 9943 |
| Feed rate, EtOH, (Kg/hr) | 1550 | 1550 |
| Feed rate, benzene & n-hexane mixture, (Kg/hr) | — | 200 |
| Oxygenate product (Kg/hr) | 3000 | 3300 |
| ETBE content in oxygenate product(Kg/hr) | 2895 | 3013.2 |
| Recycle stream flow rate (kg/hr) | 4037 | 1790 |
| Purge rate (kg/hr) | 403.7 | 179.0 |
| Residual ethanol (wt %) | 0.035 | 0.034 |
| Reboiler energy, (KW) | 5534 | 4280 |
| Condenser energy, (KW) | 5444 | 4173 |
| ENTRAINER - BENZENE | | |
| Feed rate, benzene, (Kg/hr) | — | 200 |
| Oxygenate product, (Kg/hr) | 3000 | 3300 |
| ETBE content in oxygenate product (Kg/hr) | 2895 | 3004 |
| Recycle stream flow rate (kg/hr) | 4037 | 1961 |
| Purge rate (kg/hr) | 403.7 | 196.1 |
| Residual ethanol (wt %) | 0.035 | 0.0334 |
| Reboiler energy, (KW) | 5534 | 4379 |
| Condenser energy, (KW) | 5444 | 4273 |
| ENTRAINER - n-HEXANE | | |
| Feed rate, n-hexane, (Kg/hr) | — | 200 |
| Oxygenate product, (Kg/hr) | 3000 | 3300 |
| ETBE content in oxygenate product (Kg/hr) | 2895 | 3055 |
| Recycle stream flow rate (kg/hr) | 4037 | 1925 |
| Purge rate (kg/hr) | 403.7 | 192.5 |
| Residual ethanol (wt %) | 0.035 | 0.0327 |
| Reboiler energy, (KW) | 5534 | 4371 |
| Condenser energy, (KW) | 5444 | 4264 |
| ENTRAINER - TOLUENE | | |
| Feed rate, toluene, (Kg/hr) | — | 200 |
| Oxygenate product, (Kg/hr) | 3000 | 3300 |
| ETBE content in oxygenate product (Kg/hr) | 2895 | 3023.6 |
| Recycle stream flow rate (kg/hr) | 4037 | 1432 |
| Purge rate (kg/hr) | 403.7 | 143.5 |
| Residual ethanol (wt %) | 0.035 | 0.0327 |
| Reboiler energy, (KW) | 5534 | 4042 |
| Condenser energy, (KW) | 5444 | 3935 |

Example 2

Preparation of Compositions Comprising ETBE

Following the process as disclosed in the present disclosure, three compositions comprising ETBE, and residual, but non-significant amounts of ethanol and entrainer were prepared.

Composition-1

A combination of 80 wt % benzene and 20 wt % hexane was added as an entrainer at 200 kg/hr to the binary azeotrope of ETBE/ethanol. After fractional distillation, some residual amounts of ethanol and entrainer may still be left with the ETBE which may be blended in the gasoline pool. As benzene also has a high RON value, the overall octane number of the ETBE product was maintained. Therefore, a final composition-1 comprising 91.31 wt % pure ETBE, 3.39 wt % ethanol, 4.7 wt % benzene, and 0.6 wt % n-hexane was obtained.

Composition-2

To the binary azeotrope of ETBE/ethanol, benzene was added as an entrainer and a composition-2 comprising 91.04 wt % pure ETBE, 3.34 wt % ethanol, and 5.6 wt % benzene, was obtained.

Composition-3

To the binary azeotrope of ETBE/ethanol, n-hexane was added as an entrainer and a composition-3 comprising 92.6 wt % pure ETBE, 3.27 wt % ethanol, and 4.12 wt % n-hexane, was obtained.

Advantages of the Present Disclosure

The above-mentioned implementation examples as described on this subject matter and its equivalent thereof have many advantages, including those which are described.

The present disclosure discloses a process of preparing ethyl tert-butyl ether (ETBE) which is highly demanded for adding to fuels such as gasoline to reduce its knocking properties. The present disclosure provides a group of entrainers and also allows for their combination, in order to overcome one of the most challenging aspect related to the preparation of ETBE and separation of ETBE from ethanol. The ETBE to entrainer ratio of 30:1 to 10:1, and feed rate of the entrainer in the range of 0-250 kg/hr, helps in an excellent separation of ethanol from ETBE, thereby, resulting in a highly pure ETBE product with purity greater than 91% (range 91-93%). The entrainer may also be added directly without any purge rate i.e., at zero value (0 kg/hr) of purge rate. The ETBE product having minimum quantity of residual ethanol and entrainer, produced in accordance with the present disclosure, is potential candidate for industrial applications as a fuel additive. In addition to above, the low temperature range and specific ethanol/IB ratio aids in achieving substantially improved ETBE yield of more than 69% and isobutylene conversion rates in the range 85-97%. Further, the present process is also beneficial in terms of energy efficiency as it employs low temperature conditions of 40-70° C. and the energy consumed in the subsequent reboiling and condensation is also significantly reduced. Lesser purge rates and reduced recycle stream further contribute in saving energy. Overall, the present disclosure provides for a simple, yet efficient process for preparing high quality ETBE through an energy-efficient and cost-saving route which has a promising potential to substitute the conventional methods used till now.

Although the subject matter has been described in considerable detail with reference to certain embodiments thereof, other embodiments are possible. As such, the spirit and scope of the disclosure should not be limited to the description of the embodiments contained herein.

We claim:

1. A process for the preparation of ethyl tert-butyl ether comprising:

(a) reacting ethanol with a mixture of $C_4$ hydrocarbon feed in the presence of a catalyst to obtain a mixture; and (b) contacting the mixture with an entrainer at a temperature in a range of 40-70° C. and a pressure in a range of 15-30 bars to obtain ethyl tert-butyl ether, wherein the mixture of $C_4$ hydrocarbon feed comprises isobutylene, and the ethanol to isobutylene mole ratio is in a range of 1:1 to 2:1, wherein the entrainer is a mixture of benzene and n-hexane in a volume ratio in a range of 90:10 to 40:60.

2. The process as claimed in claim 1, wherein the catalyst is selected from amberlyst 15, amberlyst 35, amberlyst 16, amberlyst 36, amberlyst 39, amberlyst 40, amberlyst 45, amberlyst 46, amberlyst 48, amberlyst DT, Purolite CT-124, Purolite CT-175, Purolite CT-275, Purolite CT-482, Purolite MN-500, aluminosilicates, H-beta zeolite, ZSM-5, ZSM-57, Lewatit K 2629, silicotungstic acid, tungstophosphoric acid, and combinations thereof.

3. The process as claimed in claim 1, wherein the process provides 85-97% conversion of isobutylene.

4. The process as claimed in claim 1, wherein the entrainer forms a low boiling azeotrope with the ethanol present in the mixture.

5. The process as claimed in claim 4, wherein the entrainer and ethanol in the mixture are recycled.

* * * * *